United States Patent [19]

Giannone

[11] Patent Number: 5,741,464

[45] Date of Patent: Apr. 21, 1998

[54] SAMPLING VALVE

[75] Inventor: Frank S. Giannone, North Bellmore, N.Y.

[73] Assignee: MMC International Corp., Inwood, N.Y.

[21] Appl. No.: 727,516

[22] PCT Filed: Apr. 17, 1995

[86] PCT No.: PCT/US95/04770

§ 371 Date: Oct. 18, 1996

§ 102(e) Date: Oct. 18, 1996

[87] PCT Pub. No.: WO95/28627

PCT Pub. Date: Oct. 26, 1995

[51] Int. Cl.[6] .................................................. G01N 1/12
[52] U.S. Cl. ............................................................. 422/103
[58] Field of Search ................................................. 422/103

[56] References Cited

U.S. PATENT DOCUMENTS 4,590,810   5/1986   Hunkin .................. 73/864.63

FOREIGN PATENT DOCUMENTS

| 185004 | 11/1906 | Germany . |
| 94 01752 | 1/1994 | WIPO . |

*Primary Examiner*—Edward J. Cain
*Attorney, Agent, or Firm*—McAulay Fisher Nissen Goldberg & Kiel

[57] ABSTRACT

A sampling tube for use in sampling a liquid or fluid, wherein a single valve is in the tube, a universal movable ball in the tube, and liquid or fluid exit at one end of the tube having an opening defining an exit port, the liquid or fluid exit at the one end of the tube including at least two legs extending from the tube having a slot between each of the two adjacent legs for the exit of liquid or fluid. The sampling tube is usable with a sampling valve and comprises a hollow tube having a base at one end for connection to a tank, the sampling tube is movable in the hollow tube for entry into the tank to obtain a sample of the contents of the tank, and the valve includes a housing and a rotatable ball having a central opening for receiving and having the sampling tube pass therethrough, the single valve comprises a mover which includes a spring-biased member for engagement with the universal movable ball and associated with the rotatable ball for moving the universal movable ball away from an end of the sampling tube to permit the liquid or fluid in the sampling tube to exit therefrom, and the fluid or liquid exiting from the sampling tube is withdrawn.

22 Claims, 3 Drawing Sheets

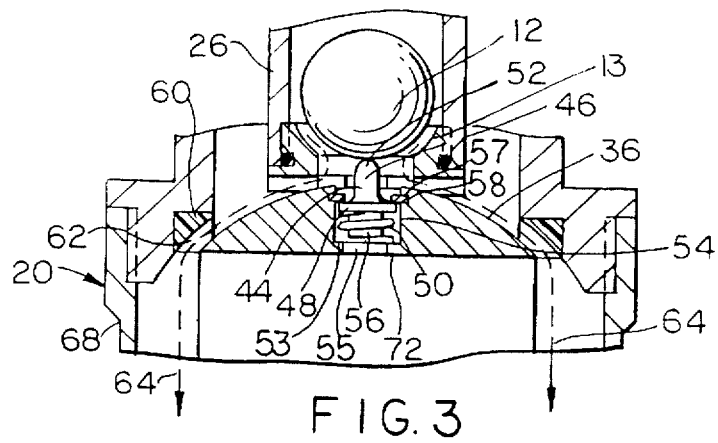
FIG.3
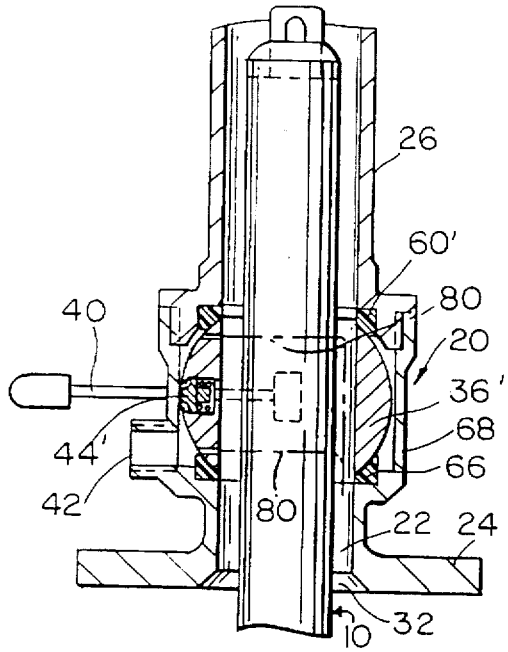
FIG.4
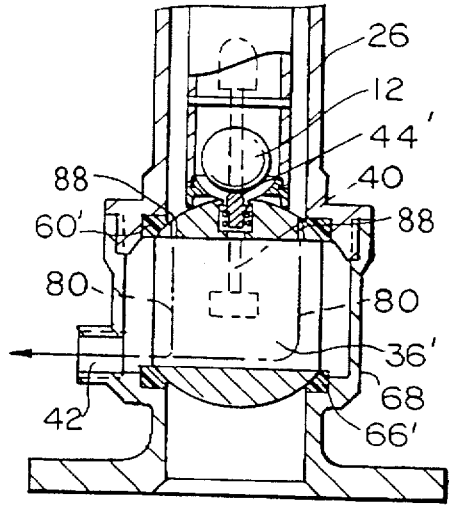
FIG.5
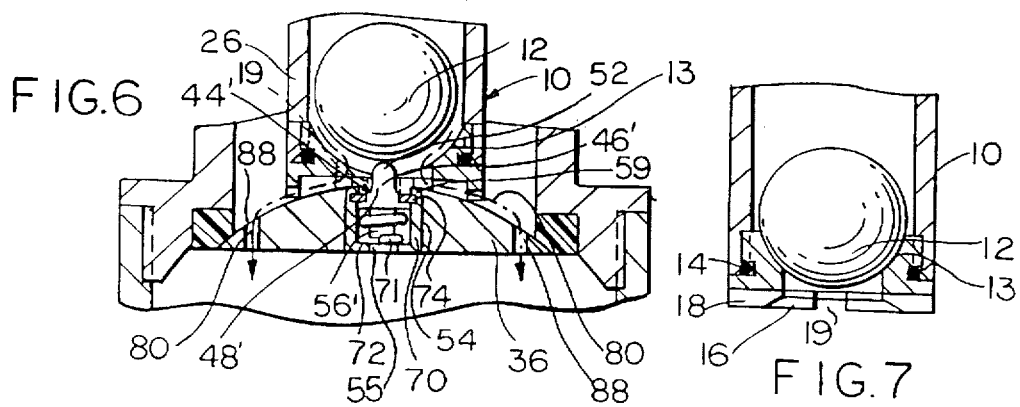
FIG.6
FIG.7

5,741,464

1

SAMPLING VALVE

TECHNICAL FIELD

This invention relates to a sampling valve. More particularly, the invention is concerned with a valve intended for use with gauging sampling tapes, and which can be used with a sampler device.

BACKGROUND ART

The prior art uses a sampling device which includes a sampler tube having an internal ball to sample a fluid or liquid. The sampler tube is conventionally lowered into a fluid or liquid, and the internal ball which closes off a bottom opening of the sampler tube rises in response to fluid or liquid pressure and allows the fluid or liquid to fill the sampler tube as the tube is lowered into the fluid or liquid product.

While it is preferred to use the sampler tube with a liquid, it is also possible to use it with all types of fluids. The sampling valve of the invention is primarily intended for use in connection with liquid handling.

Specifically, the ball itself does not float on the fluid or the liquid when a fluid or liquid is used respectively, but the ball is weighted so that, as the tube descends, into the fluid or liquid, the fluid or liquid raises the ball sufficiently so that the fluid or liquid can-pass-by the ball between the ball and the inner wall of the sampler tube. After entry of the sampler tube into the fluid or liquid for a predetermined distance, the sampling procedure is then stopped, and the ball drops down through the fluid or liquid in the sampler tube and seals the bottom of the tube to prevent any further entry of fluid or liquid into the sampler tube or exiting of the fluid or liquid from the sampler tube. In effect, the ball acts as a check valve.

Sample mechanisms to sample a fluid or a liquid are well known. One example of a prior art sampler mechanism is a sampler tube of the aforesaid type.

However, using the prior art sampler tube can produce a mess because, after the sample is taken, it then becomes necessary to drain the sample, if it is a liquid, into an open container by manually moving the ball away from the bottom of the sampler tube closure formed by the ball and bottom of the tube and allow the liquid to pour freely into an open container. If a fluid is used, perhaps another means of egress is to be used.

Another problem with the prior art sampler tube is the possibility of damage to the health of individuals using the sampler tube due to exposure to irritating liquid as well as other toxic materials vapor.

The sampling devices are generally known as zone samplers. For example, the one-liter sampler is used for use in a four-inch S valve, and there are half-liter samplers also.

DISCLOSURE OF THE INVENTION

A principle object of the present invention is to remove the liquid from the sampling tube in a more elegant manner and to eliminate any mess due to a pouring of the liquid from the sampling tube.

A further object of the invention is to provide a sampling valve having a rotatable ball in conjunction with the sampling tube.

Another object of the invention is to provide a sampling tube ball in the sampling tube which functions both as a part of a sampling valve for withdrawal of a sample of the liquid from the sampling tube and as a part of a closure for the sampling tube.

2

A feature of the invention is the elimination of a manual draining of the sampling tube and to facilitate collection of the sample.

Another feature of the invention is that a user's exposure to possible irritating liquid vapor is greatly minimized.

A further object of the invention is to provide a sampling port connected with the sampling tube.

One embodiment of the invention proposes the use of a spring-loaded button forming a part of the rotatable ball of the sampling valve and for movement of the sampling tube ball to permit exit of the sample liquid from the sampling tube.

The spring-loaded button is one feature which is built into the rotatable ball of the sampling valve of what would otherwise be a standard construction ball valve, and it is this spring-loaded button that pushes the sampler tube ball up into the sampler tube to permit the liquid or fluid to exit through the sampling valve. The liquid or fluid collected in the sampler tube can then flow through either holes drilled into one side of the rotatable ball, or through slots in the upper seal of the sampling valve, and the manner of exit flow are additional features of the invention.

The rotatable ball of the sampling valve is provided with a longitudinal opening through which the sampling tube is passed when the sampling valve is closed. The sampling tube passes through the longitudinal opening for entry from the sampling valve into a tank entry from which a sample of the contents is to be taken. The longitudinal opening is axially aligned with the tank entry and the rotatable ball when in this position closes off a port from which the sample contents of the fluid or liquid is withdrawn from the sampling tube through the sampling valve.

When the rotatable ball of the sampling valve is rotated so that the sampling tube cannot pass through the longitudinal opening, then the sampling valve is opened to permit the sample liquid or fluid to exit from the sampling valve either through the rotatable ball itself or through the slots in the upper seal of the sampling valve.

With the sampler valve opened, a sample is ready to be taken out through the sampling port of the sampler valve either through the rotatable ball or the upper seal. At this time, however, the lower seal of the ball seals off the sampling port from the tank or vessel from which the sample was taken. This procedure is preferred for a sample taken from a tank or vessel which has little or no vapor pressure.

For a tank or vessel which has been intentionally pressurized (i.e., inert gas), special care must be taken and an external control valve is needed to eliminate blow-out through an otherwise open sample port during the "sampling valve's" ball transit from the closed end to the open position. In the open position, the gauging tape attached to the thread end of the "sampling valve" prevents tank pressure blow-out from the top of the valve.

When the sample valve is used in conjunction with a "closed" or sealed hand gauging tape, a liquid or fluid sample can be taken without exposing the operator to fumes from the product. This is a special application of sampling to which the sampling valve can be applied.

BRIEF DESCRIPTION OF THE DRAWINGS

In order that the invention may be more clearly understood and readily carried into effect, the same will now be explained in connection with the accompanying drawings, in which:

FIG. 3 is an enlarged detailed view of a spring-loaded device having a pin to act on the ball sealer of the sampling valve and the upper gasket seal having one or more passageways therethrough of the check valve to allow liquid exiting from the base of the sealer tube to pass around or by-pass the rotatable ball of the sampling valve, and the spring-loaded device itself is usable in all embodiments;

FIG. 4 schematically and partially shows another embodiment of the sampling valve with the sampler tube passing through the opening in the rotatable ball of the sampling valve according to the invention, and passageways are drilled through the rotatable ball of the sampling valve for flow of the liquid or fluid from the sampling tube through an exit port from the check valve, the bottom of the conventional sampler tube being omitted;

FIG. 5 is a side view of the FIG. 4 embodiment showing liquid flow passageways through the rotatable ball and with the spring-loaded button rotated ninety degrees from its FIG. 4 position to permit the liquid to exit from the check valve through the rotatable ball to permit draining of the sample in the sampler tube, and for the sake of simplicity, certain parts in common with the sampler valve of FIGS. 1 to 3 have been omitted;

FIG. 6 is an enlarged view similar to that of FIG. 3 of the spring-loaded pin to act on the ball sealer of the sampler tube and can be used in both embodiments with the ball sealer shown in its open position raised from its sealing position to act as a seal at the bottom of the sampler tube, with the ball of the sampling valve having liquid passageways or slots cut therethrough to permit liquid or fluid to exit from the sampling device into the sampler check valve and pass through the ball of the sampling valve for exiting from the sampler tube and sampler valve;

FIG. 7 is a partial view of the sampler tube and the sampler ball closing the opening of the base end or lower end of the sampler tube; FIG. 8A illustrates an elongated tube, FIG. 8B illustrates a-one-piece ball seal with slots or passageways at the base for fluid or liquid flow, FIG. 8C is a bottom view of the one-piece ball seal, and FIG. 8D is a top view of the sampler tube.

DESCRIPTION OF THE PREFERRED EMBODIMENTS

Figure 1:
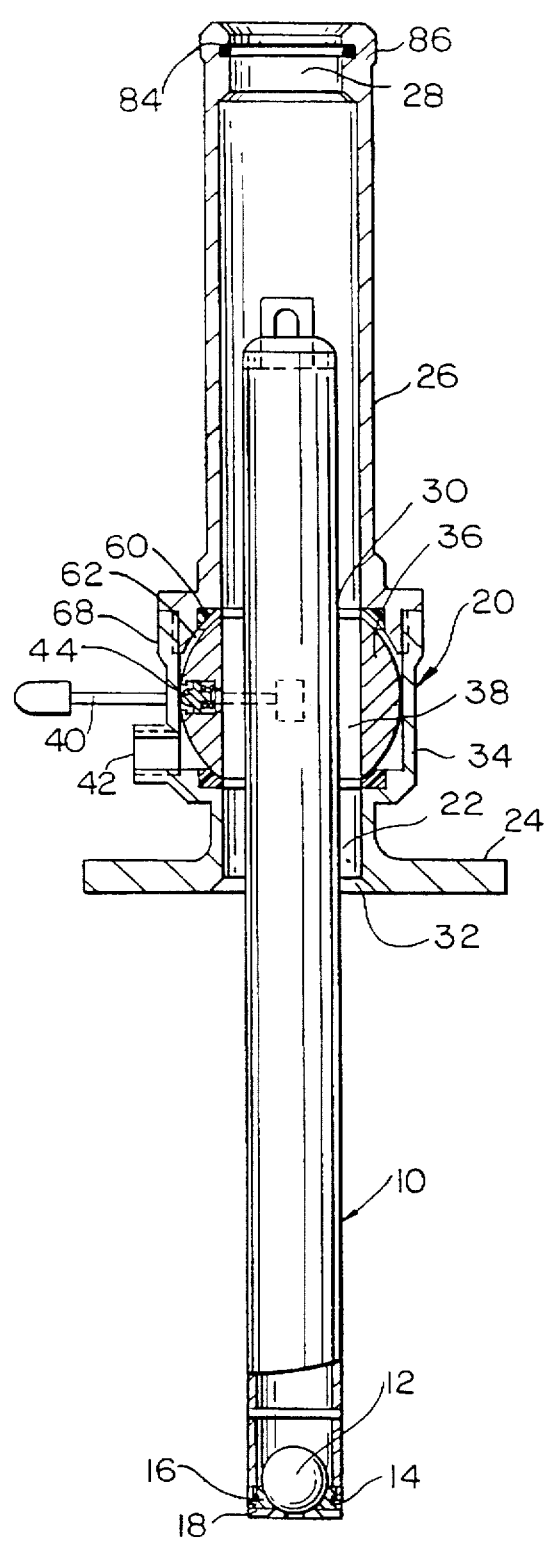
FIG. 1 schematically shows a sampler device including a sampler tube and sampler ball to close off the bottom together with a sampling check valve according to the invention having a rotatable ball with a central opening alignable with a tank opening through which the sampler device can be lowered into a tank to take a sample of the liquid in the tank and a system for removal of the liquid through slots provided in an upper seal of the novel sampling valve according to one embodiment of the invention.

Referring now more particularly to the drawings which indicate the presently preferred best modes for carrying out the invention, and in which the same parts in the different embodiments are referred to by the same reference numerals, there is shown a conventional sampler or sampling device including a sampler or sampling tube 10 having a sampler sealing axially movable ball 12 and a sealing ball seat 13 at a base or open bottom end 16 with peripherally spaced legs 18 forming slots 19 therebetween which is the first or entry end for use with a sampling valve 20 joinable to a storage tank (not shown). Between sampling tube 10 and valve seal 13, there is provided an O-ring 14, see FIGS. 7 and 8. Valve 20 includes a bottom housing forming part of an entryway 22 from base 24 for connection or coupling to a tank containing a liquid which is to be sampled. Sampler tube 10 which is provided with peripherally spaced legs 18 form therebetween the slots 19 (see FIG. 7 and FIG. 8C for detail) which form-liquid flow passageways between which the liquid exits from the sampler tube 10 when the sealer or sampler ball 12 is axially raised in sampler tube 10.

The base 24 is adapted to be connected by conventional means with the tank (not shown) and includes the sampling valve 20 extending from the top thereof remote from base 24, a hollow vertical tube 26 through which the sampler or sampling tube 10 of the sampling device passes. The hollow vertical tube 26 includes an entryway 28 and an exitway opening 30 opening to sampling valve 20. The base 24 has a central opening 32 which opens into the tank when base 24 is either connected to the tank by means not shown or rests on the tank. As shown, hollow vertical tube 26 has a longitudinal axis which coincides substantially with the longitudinal axis of the sampler tube 10 and vertical tube 26. exitway opening 30 and central opening 32 are axially aligned.

Sampling valve 20 includes a valve housing 34 for housing a rotatable ball 36 having a central opening 38 coaxial with, in one portion thereof, the closed condition of valve 20, the vertical or longitudinal axis of the hollow vertical tube 26 through which the sampling tube 10 of the sampling device passes from the sampler valve for entry into the tank for sampling purposes. Handle 40 is shown in a horizontal position in FIG. 1 of the drawing for aligning opening 38 of rotatable ball 36 with the hollow vertical tube 26 to permit the sampler tube 10 to pass completely through opening 38 of the rotatable ball 36, and then through opening 32 and into the tank (not shown). In this position, the sampling tube 10 of the sampling device can be inserted into the tank and can take a sample. Handle 40 shown in the horizontal position in FIG. 1, in a second position, which is the open condition of valve 20 and is used to rotate the rotatable ball 36 through an angle of 90° clockwise from its open condition to its closed condition to the horizontal position for central opening 38 shown in FIG. 2 transverse to the longitudinal axis of the sampler tube 10 and hollow vertical tube 26 after the sampler tube 10 is withdrawn from the tank (not shown) and withdrawn from rotatable sampling valve ball 36 and central opening 38, to close off the entryway to the tank through the rotatable sampling valve ball 36, and to rotate the ball 36 counter-clockwise to align the central ball opening 38 axially with the longitudinal axis of vertical tube 26 so as to receive the sampling tube 10 for insertion into the tank.

Valve 20 also includes a main exit port 42 through which the liquid sample can be taken after it exits from sampler tube 10 and passes through sampling valve 20. Exit port 42 may also be provided with a separate closure (not shown) to control exiting of the sample fluid or liquid from the exit port 42.

When a sampling valve according to the invention is used, it is possible to provide a special sampling port or other exit ports similar to exit port 42 which is a flow path connected with the sampling tube, and any conventional control valve or hose can also be connected with the sampling port.

Figure 2:
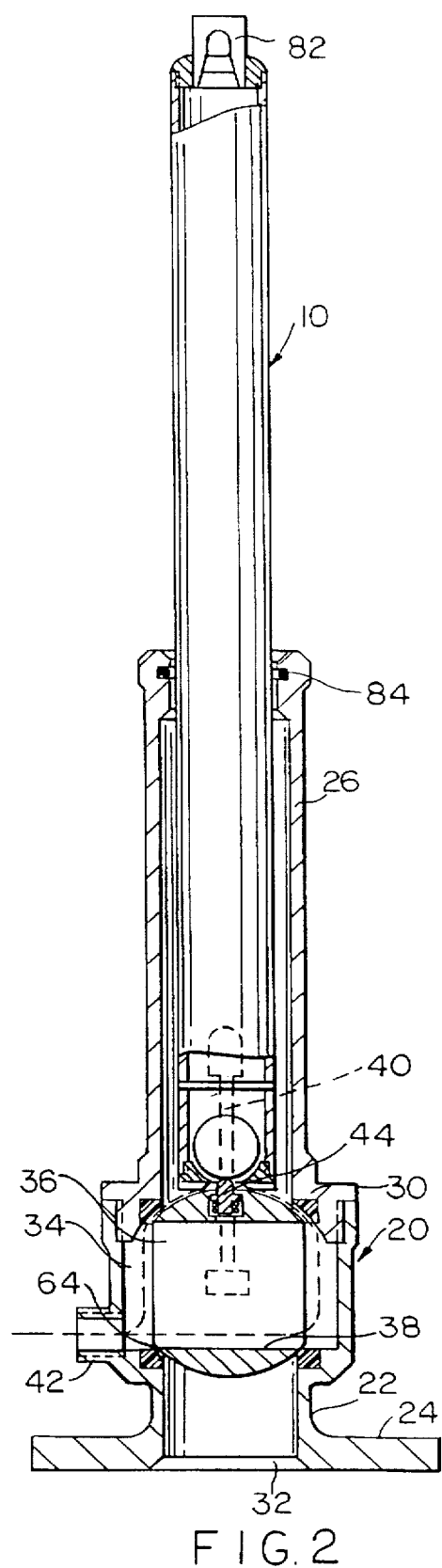
FIG. 2 shows another view of the FIG. 1 embodiment with the sampler tube shown in its raised position after a sample has been taken and a spring-loaded button in engagement with the sampler ball sealer or sampler ball of the sampler tube for raising the sampler ball or moving the sampler ball away from the base of the sampler tube and to allow the fluid or liquid to pass out of a port of the check valve, after it passes through the slots in the upper seal of the sampling valve.

The rotatable ball has coupled therewith a spring-loaded mechanism 44 shown at a 90° angle displacement from the axis of the vertical tube 26 and orthogonal to central opening 38, see FIGS. 1 and 4. In FIG. 2, spring-loaded mechanism 44 has been rotated clockwise through an angle of 90° for axial alignment with the longitudinal axis of tube 10.

The spring-loaded mechanism 44 is shown orthogonal to central opening 38. However, all that is required is that mechanism 44 be provided so that when sampler tube is withdrawn from central opening 38, the rotatable sampling valve ball 36 can be rotated and provide cooperative action between sampler sealing ball 12 and mechanism 44 so that sealing ball 12 can be moved axially upwards in tube 10 to provide for the sampling liquid to exit from tube 10.

Referring now more particularly to FIG. 3, the sampler tube 10 is shown raised in a position above rotatable ball 36 but resting thereon, and as shown ball 36 has been rotated clockwise through an angle of 90° because of the particular placement of the spring load and to move spring-loaded device 44 to a position axially aligned with the axes of hollow vertical tube 26 and sampler tube 10.

Spring-loaded mechanism or device 44 is received within U-shaped recess in rotatable ball 36 and includes a pusher member 46 having a piston-type base 48 to cooperate with a compression spring 50 and a tip or pin portion 52 extending from piston-type base 48 for engagement with the sampler or sealer ball 12 of the sampling device. Compression spring 50 seats in recessed opening 54 provided in or cut into rotatable ball 36. The recessed opening 54 includes an opening or drain hole 55 forming a fluid or liquid drain hole which is connected with the main exit port 42 through a passageway in the rotatable ball 36 formed by central opening 38. Piston-type base 48 is provided with a center post 56 about which compression spring 50 surrounds and is aligned with pin 52 of pusher member 46 for guiding of pin 52 into engagement with the outer surface of sampler sealing ball 12 and exerts pressure against the base of pusher member 48 for causing pin 52 to be engaged with the surface of ball 12 and to move or raise ball 12 vertically away from the ball seat 14 at the base of sampler tube 10 to allow the liquid to exit from the sampler tube 10 through openings or liquid flow passageways 19 between peripheral legs 18. Compression spring 50 has one end bearing against the underside of pusher member 48 and the other side bearing against the base 53 of recessed opening 54. Spring type washer 58 is received in recessed portion 59 and is spring urged into recessed portion 59 for holding spring 50 and pusher member together.

In this embodiment as shown in FIG. 3, sampling valve 20 includes an upper ball seat 60 preferably formed from TEFLON® having passageways 62 cut through to allow the liquid to pass around the ball 36 when the ball is rotated 90° clockwise after the sampling tube 10 is moved out of the sampling valve and moves through pathways 64 in sampling valve 20 as generally indicated by the dashed line. The liquid flows out of sampler tube 10 through the passageways 19 between legs 18, through passageways 62 and pathways 64 to exit through main exit port 42.

A downstream seal or ball seat 66 is used to provide the appropriate sealing, but no pathway is cut through ball seat 66, and TEFLON® seats or gaskets 60 and 66 are housed within housing 68 of sampling valve 20.

Referring now more particularly to FIGS. 4 to 6 which illustrate the second embodiment in which the same reference numerals designate the same elements in FIGS. 1 to 3 of the drawings, and variant embodiments use the same reference numeral, but primed.

In this embodiment, rotatable ball 36 is also rotatable through an angle of 90° clockwise or less, as desired depending on the construction, from the FIG. 4 position to the FIG. 5 position to align spring-loaded device 44' to a position axially aligned with the axis of hollow vertical tube 26.

In this embodiment, spring-loaded device 44' includes a separate unitary element having a U-shaped casing member 70 receivable within the recessed opening 54 in rotatable ball 36' and includes a center post 56'. Casing member 70 includes a recessed portion 59' for receiving a spring-type washer 58 for holding pusher member 46' against compression spring 50. Compression spring 50 is positioned about center post 56' in a manner similar to that of FIG. 3, and pusher member 46' includes a piston-type base 48' which together with casing member 70 acts as a guideway for the movement of pusher member 46' in a vertical direction towards and away from sampler ball 12.

Casing member 70 facilitates insertion of spring-loaded device 44' as a unit into the recessed opening 54. Casing member 70 includes an opening 71 which opens to opening or drain hole 55.

Referring to FIG. 8, the sampling tube 10 includes a base portion having an internal thread 72 (FIG. 8A), and a one-piece ball seat 74 (FIG. 8B) having an outer threaded portion 76 for receiving the ball seat 74 at the portion with the internal threads 72. The ball seat includes the spaced legs 18 which have the slots 19 between each pair of legs 18. A ball stop cross-pin 78 is provided to prevent the ball from progressing too high up the column of sampling tube 10.

Figure 8D:
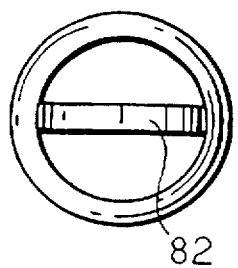
FIGS. 8A, 8B, 8C and 8D illustrate a sampling tube.
Figure 8A:
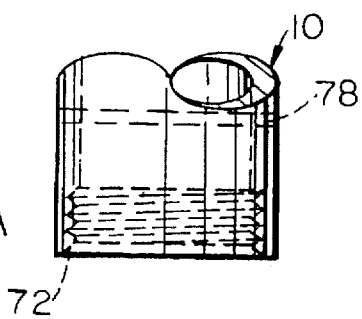
Figure 8B:
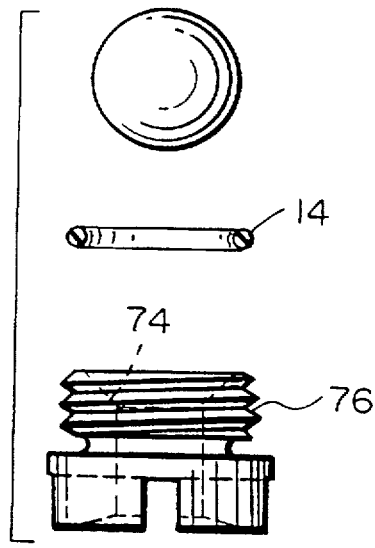
Figure 8C:
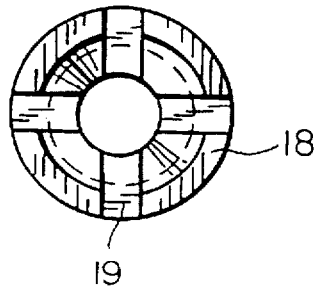

The top portion of the sampling tube 10 as best seen in FIG. 8d includes an open top 80 having a holder or support 82 extending across the top of the sampler tube 10 for holding, carrying and support thereof and leaving an opening at the top for exit of air as the liquid is drawn into the sampler tube.

The hollow vertical tube 26 on the inner portion thereof at the top is provided with an O-ring 84 when it is withdrawn for sealing with the sampler tube 10, and at the outer portion thereof, the holder or support 82 acts as a connection portion for ease of removal of the sampling valve 20 from the tank.

For the FIGS. 1 to 3 embodiment, specific reference was made to the slotting of the upstream seal or TEFLON® ball seal or seat 60 or equivalent. No detailed discussion was made of the downstream ball seal or seat or gasket 66, and the downstream gasket or ball seat 66 in the sampling valve is a conventional seal and preferably a TEFLON® seat. This is shown on the drawing as well as referred to in the specification.

For the FIGS. 4 to 6 embodiment, both the downstream ball seal or seat 66' and the upstream ball seal or seat 60' are the same and are not provided with passageways and are preferably formed from TEFLON® or equivalent.

In this embodiment, instead of providing passageways 62 through upper ball seat 60, the fluid or liquid flows through slots or passageways 19 provided between spaced legs 18 through the central opening 38 from one or more fluid or liquid pathways 88 which are cut into rotatable ball 36' so that fluid or liquid from the sampler tube 10 can pass through the pathways or passageways 88 and through the central opening 38 as schematically shown by dashed flow pathway lines 80 in FIGS. 4 to 6 when the ball 36 is rotated from its FIG. 4 position to its FIG. 5 position. When the tip or pin portion 52 is aligned with the sampler ball 12 it is moved away from the opening and the liquid can pass through passageways 88 and along the pathway 80 through central opening 38 and out of port 42. Also, liquid which exits from opening 71 and through opening 55 (see FIG. 6) into the central opening merges with the liquid or fluid flowing through passageways 88. These passageways 88, as noted heretofore, are cut through the surface of rotatable ball 36' and through the ball and into central opening 38.

In the FIGS. 1 to 3 embodiment, the liquid which flows through opening or drain hole 55, such liquid can flow out either through passageways similar to passageways 88 or through a passageway (not shown) directly into central opening 38 or the liquid can flow directly from drain hole 55 as shown into central opening 38.

INDUSTRIAL APPLICATION

The sampling tube 10 includes the holder or support 82 which is used as an attachment or connector portion for connection with a tape (not shown) of a closed sampling tube. Hollow vertical tube 26 includes an outside connector ring 86 for connection with the housing (not shown) of a sampling tube assembly.

With respect to the sampling valve and sampler tube 10 and the sampler ball 12, the liquid or fluid pressure in the tank from which a sample is taken must be sufficient to raise the ball 12 between the legs 18 above the inlet; by the same token, the fluid or liquid pressure in sampler tube 10 and the weight of the ball is sufficient to seat the ball 12 at the outlet of the sampler tube 10 after a sample is taken.

The sampling valve uses a standard ball valve, and the 90° turn merely is a one-quarter turn, and as noted heretofore, a turn of lesser or greater than 90° will be operative.

The base of the sampler tube, as noted, includes legs so that there is spacing or slots 19 between the base of the sampler tube and the legs. The liquid would then run out between the base of the sampler tube and the sampler ball valve after the sampler ball is raised and prevent clogging.

While hollow vertical tube 26 and base 24 are shown integral and formed as a unit as part of the sampling valve 20, these may be separate elements which are connectable together with the valve housing 34.

I claim:

1. A sampling valve for use with a sampling device having a sampler tube and a sampler ball to close off an end of the sampler tube which is adapted to enter a tank to obtain a sample of the contents of the tank, said valve comprising:
   a housing and a rotatable ball in said housing, said rotatable ball having a central opening for receiving and having the sampler tube pass therethrough;
   moving means including spring-biased means for engagement with said sampler ball associated with said rotatable ball for moving said sampler ball away from an end of said sampler tube to permit the liquid or fluid in said sampler tube to exit therefrom; and
   means for withdrawing the fluid or liquid exiting from said sampler tube.

2. The sampling valve according to claim 1, wherein said withdrawing means includes an upstream ball seat in said housing having pathways cut thereinto to permit the liquid or fluid to flow between said rotatable ball and said ball seat.

3. The sampling valve according to claim 1, wherein said moving means includes an opening in said rotatable ball, engagement means receivable within said opening for engagement with said sampler ball, a post connected with said engagement means and a compression spring guided by said post towards said sampler ball for moving said sampler ball away from the end of said sampler tube.

4. The sampling valve according to claim 3, wherein said means for withdrawing includes an upstream ball seat in said housing having pathways cut thereinto to permit the liquid or fluid to flow between said rotatable ball and said ball seat.

5. The sampling valve according to claim 1, wherein said means for withdrawing includes pathways cut into said rotatable ball through which the liquid or fluid from said sample tube passes.

6. The sampling valve according to claim 1, wherein said means for withdrawing includes an opening in said rotatable ball for receiving said spring-biased means, and an opening communicating with an exit from the sampler tube through which liquid or fluid from the sampler tube passes by the spring-biased means through said rotatable ball.

7. The sampling valve according to claim 1, wherein said means for withdrawing includes at least one pathway cut through said rotatable ball through which the liquid or fluid exiting from said sample tube passes.

8. The sampling valve according to claim 1, wherein said moving means includes a casing member having a base and a pusher member having a center post extending substantially orthogonally therefrom, and a compression spring having one end in contact with said base and the other end in contact with said pusher member for urging said pusher member into engagement with the sampler ball, and said rotatable ball having a central opening for receiving said casing member.

9. The sampling valve according to claim 8, including a spring washer receivable in said casing for holding said pusher member against said spring in said casing member.

10. The sampling valve according to claim 8, wherein said means for withdrawing includes an upstream ball seat in said housing having at least one pathway cut thereinto to permit the liquid to flow between said rotatable ball and said ball seat.

11. The sampling valve according to claim 8, wherein said casing member includes in the base thereof a casing opening through which the liquid or fluid from said sample tube passes and said rotatable ball includes an opening through which said liquid or fluid passes after exiting from said casing opening.

12. The sampling valve according to claim 1, including an exit port coupled with said housing for withdrawing the liquid or fluid exiting from said sampler tube and moving through said housing for exiting from said exit port.

13. The sampling valve according to claim 11, including an exit port coupled with said housing for withdrawing the liquid exiting from said sampler tube and moving through said housing for exiting from said exit port.

14. The sampling valve according to claim 1, including means associated with said housing for coupling thereof to a tank in which the liquid is to be sampled, said last-mentioned means having an opening for passage therethrough of the sampling device, and said rotatable ball being movable from a position of said opening to a position closing off said opening.

15. A sampling tube for use in sampling a liquid or fluid, comprising a tube and a single valve in the tube, a universal movable ball in said tube, and liquid or fluid exit means at one end of said tube having an opening defining an exit port, said liquid or fluid exit means at said one end of said tube including at least two legs extending from said tube having a slot between each said two adjacent legs for the exit of liquid or fluid.

16. The sampling tube according to claim 15, wherein said exit port includes a plurality of legs and a slot between each pair of adjacent legs.

17. The sampling tube according to claim 15, including an opening at the other end of said tube free of any closure and a holder for said tube at said other end.

18. The sampling tube according to claim 15, including a sealing ball seat at said one end of said tube which together with said movable ball closes off said exit port.

19. A sampling tube for use in sampling a liquid or a fluid, comprising a tube having an opening at each end and a valve characterized in that there is only a single valve in the tube for closing and opening only one end of the tube which comprises a universal movable ball in said tube for closure of only one end of the tube to form a single liquid or fluid entrance and exit device solely at said one end of said tube for defining an opening defining an entrance way and an exit port and free of any closure of said other end of the tube, the liquid or fluid entrance and exit device at said one end of said tube including at least two legs and a slot between each said two adjacent legs for the exit of liquid or fluid, and a ball stop cross pin connected within said tube to control the extent sand ball moves towards said other end as liquid or fluid enters into said tube through the one end.

20. The sampling tube according to claim 19, wherein said entrance way and exit port includes a plurality of legs and a slot between each two said adjacent legs.

21. The sampling tube according to claim 19, including a holder or support for the tube at the other end extending across the tube without closure thereof.

22. The sampling tube according to claim 19, including a sealing ball seat in said tube at said one end which together with said movable ball closes off said entrance way and exit port.

* * * * *